US010406505B1

(12) United States Patent
Robb et al.

(10) Patent No.: US 10,406,505 B1
(45) Date of Patent: Sep. 10, 2019

(54) COATINGS (71) Applicant: VENATOR MATERIALS UK LIMITED, Stockton-on-Tees Durham (GB)

(72) Inventors: John Robb, Stockton-on-Tees (GB); Ann Sarah Wan, Stockton-on-Tees (GB); Karl Lowry, Stockton-on-Tees (GB); Darren J. Waters, Brotton (GB); John L. Edwards, Durham (GB)

(73) Assignee: VENATOR MATERIALS UK LIMITED, Stockton-on-Tees Durham (GB)

( * ) Notice: Subject to any disclaimer, the term of this patent is extended or adjusted under 35 U.S.C. 154(b) by 0 days.

(21) Appl. No.: 15/777,215

(22) PCT Filed: Nov. 17, 2016

(86) PCT No.: PCT/GB2016/053591
§ 371 (c)(1),
(2) Date: May 18, 2018

(87) PCT Pub. No.: WO2017/085493
PCT Pub. Date: May 26, 2017

(30) Foreign Application Priority Data

Nov. 20, 2015 (GB) .................................. 1520463.9

(51) Int. Cl.
*B01J 21/06* (2006.01)
*B01J 31/38* (2006.01)
(Continued)

(52) U.S. Cl.
CPC .......... *B01J 21/063* (2013.01); *B01D 53/007* (2013.01); *B01D 53/8628* (2013.01);
(Continued)

(58) Field of Classification Search
CPC ..... A61L 9/00; A61L 9/01; A61L 9/20; A61L 9/205; A61L 2209/00; A61L 2209/10;
(Continued)

(56) References Cited

U.S. PATENT DOCUMENTS

| 5,853,866 A | 12/1998 | Watanabe et al. |
| 6,699,577 B2 * | 3/2004 | Nonoyama ........ B01D 53/8637 428/323 |

(Continued)

FOREIGN PATENT DOCUMENTS

| CN | 101 418 151 A | 4/2009 |
| CN | 104 843 786 A | 8/2015 |

(Continued)

OTHER PUBLICATIONS

M.M. Ballari et al.: "$NO_x$ photocatalytic degradation employing concrete pavement containing titanium dioxide", Applied Catalysis B: Environmental, vol. 95, pp. 245-254 (2010).
(Continued)

*Primary Examiner* — Timothy C Vanoy
(74) *Attorney, Agent, or Firm* — Norman B. Thot (57) ABSTRACT

The present invention provides a coating composition suitable for use in forming a coating that can reduce a concentration of pollutant gases in the environment. The coating composition includes from 0.01 to 10 vol.-% of mesoporous titania particles, relative to a total volume of the coating composition, and from 5 to 99.99 vol.-% of a polymeric material, relative to the total volume of the coating composition. The mesoporous titania particles have a continuous exterior convex surface, a particle diameter of ≥1 μm but ≤ to 50 μm, a BET specific surface area of from 30 to 350 m²/g, a modal pore diameter of ≥5 nm but ≤50 nm, and a
(Continued)

pore size distribution so that 85% or more of a total pore volume is associated with pores having a diameter of 10 µm or less.

33 Claims, 1 Drawing Sheet

(51) Int. Cl.

| | | |
|---|---|---|
| *B01J 31/06* | (2006.01) | |
| *B01J 35/00* | (2006.01) | |
| *B01J 35/10* | (2006.01) | |
| *B01J 21/08* | (2006.01) | |
| *B01J 35/08* | (2006.01) | |
| *B01J 37/02* | (2006.01) | |
| *B01J 37/00* | (2006.01) | |
| *B01D 53/00* | (2006.01) | |
| *B01D 53/86* | (2006.01) | |
| *B01D 53/88* | (2006.01) | |
| *B01J 35/02* | (2006.01) | |

(52) U.S. Cl.
CPC ....... *B01D 53/8687* (2013.01); *B01D 53/885* (2013.01); *B01J 21/08* (2013.01); *B01J 31/06* (2013.01); *B01J 31/38* (2013.01); *B01J 35/004* (2013.01); *B01J 35/026* (2013.01); *B01J 35/08* (2013.01); *B01J 35/1014* (2013.01); *B01J 35/1019* (2013.01); *B01J 35/1042* (2013.01); *B01J 35/1061* (2013.01); *B01J 35/1085* (2013.01); *B01J 37/0018* (2013.01); *B01J 37/0219* (2013.01); *B01J 37/0244* (2013.01); *B01D 2255/20707* (2013.01); *B01D 2255/802* (2013.01); *B01D 2255/9202* (2013.01); *B01D 2255/9207* (2013.01)

(58) Field of Classification Search
CPC ............. A61L 2209/13; A61L 2209/20; A61L 2209/21; A61L 2209/22; B01D 2221/16; B01D 2252/602; B01D 2253/1124; B01D 2253/25; B01D 2253/30; B01D 2255/20707; B01D 2255/802; B01D 2255/90; B01D 2255/92; B01D 2258/06; B01D 2259/804; B01J 15/005; B01J 20/0211; B01J 20/285; B01J 21/063; B01L 35/00; B01L 35/002; B01L 35/004; B01L 35/0046; B01L 37/00
See application file for complete search history.

(56) References Cited

U.S. PATENT DOCUMENTS

| | | | |
|---|---|---|---|
| 8,691,144 B2 * | 4/2014 | Garfield | ................ A61L 9/205 252/514 |
| 10,201,809 B2 * | 2/2019 | Ozaki | ..................... B01J 35/02 |
| 2006/0257312 A1 | 11/2006 | Torardi | |
| 2009/0239742 A1 | 9/2009 | Vanderspurt et al. | |
| 2013/0160837 A1 | 6/2013 | Ting et al. | |
| 2016/0236174 A1 | 8/2016 | Lowry et al. | |

FOREIGN PATENT DOCUMENTS

| | | | | |
|---|---|---|---|---|
| JP | H11 226422 A | | 8/1999 | |
| JP | 2006 232865 A | | 9/2006 | |
| JP | 2010 150434 A | | 7/2010 | |
| WO | WO-2007143017 A1 | * | 12/2007 | ............ A61L 9/205 |
| WO | WO-2015040426 A1 | * | 3/2015 | ............ B01J 21/063 |

OTHER PUBLICATIONS

S. Brunauer et al.: „Adsorption of Gases in Multimolecular Layers, J. Am. Chem. Soc., vol. 60, pp. 309-319 (1938).
International Standard ISO 22197-1: „Fine ceramics (advanced ceramics, advanced technical ceramics)—Test method for air-purification performance of semiconducting photocatalytic materials pp. 1-17 (2007).

* cited by examiner

COATINGS

CROSS REFERENCE TO PRIOR APPLICATIONS

This application is a U.S. National Phase application under 35 U.S.C. § 371 of International Application No. PCT/GB2016/053591, filed on Nov. 17, 2016 and which claims benefit to Great Britain Patent Application No. 1520463.9, filed on Nov. 20, 2015. The International Application was published in English on May 26, 2017 as WO 2017/085493 A1 under PCT Article 21(2).

FIELD

The present invention relates to coatings comprising mesoporous titania particles and their use in removing pollutant gases.

BACKGROUND

In recent years the pollution of air, water and/or soil has become a key issue, especially in urban areas. Two of the major classes of environmental polluting substances are nitrogen oxides (NOx) and volatile organic compounds (VOCs). These compounds are, in particular, considered as undesirable because they initiate the formation of secondary polluting substances.

Various solutions have been proposed to reduce the concentration of air polluting substances in the environment.

The photocatalytic properties of titanium dioxide ($TiO_2$) are well known. Titanium dioxide activates with ultraviolet (UV) radiation to oxidize air pollutants, such as nitrogen oxides and volatile organic compounds. Therefore titanium dioxide has been employed to remove harmful NOx gases (NO and $NO_2$) from the atmosphere, by oxidation to nitrates.

For example, applying titania particles to pavement can help to remove emission pollutants right next to the source, i.e., near the vehicles. The degradation of nitrogen oxides by concrete paving stones that contain titania has been studied and is described in M. M. Ballari et al. *Applied Catalysis B: Environmental*, 95, (2010), 245-254.

Photocatalytic surfaces containing titania particles, e.g., paints or plastic coatings, promote NOx removal by photodestructive radical mechanisms. Therefore, related photodestruction of other materials in the coating, especially polymers, has been an unavoidable consequence. These photocatalytic properties of titanium dioxide particles therefore result in very short lifetimes for coatings containing the titania.

To date, it has been difficult to provide coatings having high levels of titanium dioxide photocatalyst because the catalyst tends to oxidize and break down polymeric material (e.g., binder) in the coating. This problem is exacerbated when the coating is exposed to intense UV radiation from sunlight, as is the case with an exterior paint.

For exterior paints, their activity in terms of ability to remove pollutant gases may be reduced after weathering.

Equally, for exterior paints, significant weight loss will normally occur after weathering, due to the titania breaking down the polymeric binder of the paint. Gloss loss and color fade (in non-white surfaces) are more evident symptoms of degradation.

Thus it has been identified by the inventors that there is a need for coating compositions which can exhibit excellent surface de-polluting properties without the coating undergoing significant photodegradation.

It would be desirable for these characteristics to be present regardless of the environment to which the coatings are exposed. Thus they should be present both for coatings that are used indoors and for coatings that are exposed to intense UV radiation from direct sunlight.

SUMMARY

An aspect of the present invention is to provide coatings, such as paints, which have long coating lifetimes when exposed to light and which provide excellent pollutant gas removal.

In an embodiment, the present invention provides a coating composition suitable for use in forming a coating that can reduce a concentration of pollutant gases in the environment. The coating composition includes from 0.01% to 10% by volume of mesoporous titania particles, relative to a total volume of the coating composition, and from 5% to 99.99% by volume of a polymeric material, relative to the total volume of the coating composition. The mesoporous titania particles comprise a continuous exterior convex surface, a particle diameter of greater than or equal to 1 μm but less than or equal to 50 μm, a BET specific surface area of from 30 $m^2$/g to 350 $m^2$/g, a modal pore diameter of greater than or equal to 5 nm but less than or equal to 50 nm, and a pore size distribution so that 85% or more of a total pore volume is associated with pores having a diameter of 10 microns or less.

BRIEF DESCRIPTION OF THE DRAWING

The present invention is described in greater detail below on the basis of embodiments and of the drawing in which.

DETAILED DESCRIPTION

The present disclosure provides, in a first aspect, a coating composition suitable for use in forming a coating that can reduce the concentration of pollutant gases in the environment, the coating composition comprising polymeric material together with mesoporous titania particles, wherein the particles have a continuous exterior convex surface, and a particle diameter of greater than or equal to 1 μm but less than or equal to 50 μm, and a BET specific surface area of from 30 $m^2$/g to 350 $m^2$/g, and a modal pore diameter of greater than or equal to 5 nm but less than or equal to 50 nm, and a pore size distribution such that 85% or more of the total pore volume is provided by pores with a diameter of 10 microns or less, wherein the coating composition comprises from 0.01% to 10% by volume of the particles, relative to the total volume of the coating composition, and comprises from 5% to 99.99% by volume of polymeric material, relative to the total volume of the coating composition.

Surprisingly, a coating formed from such a coating composition is effective at reducing the concentration of pollutant gases in the environment, e.g., from air or water near to the coating, and even after weathering (including exposure to intense UV radiation from sunlight) the coating does not experience significant weight loss, color fade or gloss deterioration. This indicates that the provision of the titania in this specific particulate form is such that the titania is not efficiently providing radicals to the coating and so is not breaking down the polymeric material.

It may be that the coating composition is provided as a kit that comprises a first part which is a coating base comprising polymeric material and, optionally, one or more further coating composition components, such as carrier or solvent or additives, and a second part that is the mesoporous titania particles. The first part and the second part can be mixed together to form a mixture that is then applied to a surface as a layer. Alternatively, the first part can be applied to a surface as a first layer and the second part can be applied as a second layer (e.g., by dusting the second part on top of the first layer, or by lamination of the second part on top of the first layer, or by coextrusion of the two parts to form the two layers). In each case, a coating is provided on the surface that comprises polymeric material and mesoporous titania particles (and, optionally, one or more further coating composition components, such as carrier or solvent or additives).

The present disclosure provides, in a second aspect, a coating formed from the coating composition as described in the first aspect of this disclosure, wherein the mesoporous titania particles are either dispersed within the coating or are present as a layer at the exterior face of the coating.

The coating is suitably provided on a surface that is, in use, exposed to an environment containing pollutant gases. The surface may be one that is exposed to such an environment or may be a surface that will be exposed to such an environment. The exterior face of the coating is the face that is exposed to the environment containing pollutant gases.

The coating is suitably provided on a surface that is, in use, exposed to UV radiation from sunlight or UV radiation from an artificial source, such as a fluorescent bulb.

The present disclosure provides, in a third aspect, a process for providing a coating on a surface, the coating being suitable for use in reducing the concentration of pollutant gases in the environment, the process comprising:
  a) providing a coating base comprising polymeric material and, optionally, one or more further coating composition components, such as carrier or solvent or additives;
  b) applying the coating base to a surface, to form a layer; and
  c) applying mesoporous titania particles to the layer, thereby forming a coating comprising the coating base and the particles;
wherein the particles have a continuous exterior convex surface and a particle diameter of greater than or equal to 1 μm but less than or equal to 50 μm, and a BET specific surface area of from 30 $m^2$/g to 350 $m^2$/g, and a modal pore diameter of greater than or equal to 5 nm but less than or equal to 50 nm, and a pore size distribution such that 85% or more of the total pore volume is associated with pores with a diameter of 10 microns or less, wherein the coating comprises from 0.01% to 10% by volume of the particles, relative to the total volume of the coating and comprises from 5% to 99.99% by volume of polymeric material, relative to the total volume of the coating.

It may be that the mesoporous titania particles are applied to the layer by dusting the particles onto the layer. It may be that the mesoporous titania particles are applied to the layer by laminating the particles onto the layer. It may be that the mesoporous titania particles are coextruded with the coating base onto the surface, so as to form a layer of the coating base on the surface and a layer of the mesoporous titania particles on top of that layer.

The present disclosure provides, in a fourth aspect, a process for providing a coating on a surface, the coating being suitable for use in reducing the concentration of pollutant gases in the environment, the process comprising:
  i) providing a coating composition as defined in the first aspect; and
  ii) applying the coating composition to a surface, to form a layer.

It may be that in step i), the coating composition as provided is one where the mesoporous titania particles are mixed with the polymeric material; for example, the particles may be uniformly dispersed within the coating composition.

It may also be that in step i), the coating composition as defined in the first aspect is provided by initially providing a coating base comprising polymeric material and then dispersing the mesoporous titania particles in the coating base, to form a coating composition.

The coating base as initially provided may optionally comprise one or more further coating composition components, such as a carrier or solvent or additives.

In an embodiment, after the mesoporous titania particles have been dispersed in the coating base material, one or more further coating composition components can, for example, be added. These may then be dispersed in the coating base material.

The present disclosure provides, in a fifth aspect, an article having an exterior surface, at least part of the exterior surface being coated with a coating formed from a composition as defined in the first aspect.

This article can, for example, have at least part of its exterior surface coated with a coating as defined in the second aspect.

It may be that the article is obtained by carrying out the process of the third aspect or the process of the fourth aspect.

The article may, for example, be a building or a part thereof, such as a roof or a door or a window frame. However, the present disclosure is not limited to such articles.

Other articles that may be considered include, but are not limited to, pavements, automobiles, road surfaces, aircraft, water vessels including boats and ships, signs, fencing, decking, sound-barriers and railings.

An article can, for example, in use, have at least one surface that is exposed to both pollutant gases and to UV radiation (e.g., from sunlight).

The present disclosure provides, in a sixth aspect, a method for removing pollutant gases from the environment, the method comprising the steps of:
  providing an article as defined in the fifth aspect; and
  allowing the coated surface to contact the environment that contains pollutant gases.

In particular, the method may be used for the removal of pollutant gases from the environment in external conditions, and especially conditions where the coating is exposed to UV radiation from sunlight.

The method may, in an embodiment, be used, for example, for the removal of pollutant gases in external conditions, and especially conditions where the coating is exposed to UV radiation (e.g., from sunlight) over the long term, e.g., over time frames of 1000 hours or more, or 2000 hours or more, or 5000 hours or more, e.g., 10,000 hours or more, or 20,000 hours or more, or 50,000 hours or more.

It may therefore be that the coated surface is allowed to contact the environment over the long term, e.g., over time frames of 1000 hours or more, or 2000 hours or more, or 5000 hours or more, e.g., 10,000 hours or more, or 20,000 hours or more, or 50,000 hours or more.

In an embodiment, the step of providing an article can, for example, involve carrying out the process of the third aspect or carrying out the process of the fourth aspect.

In a seventh aspect, there is provided the use of the coating as described in the second aspect of the disclosure or the article as described in the fifth aspect of the disclosure for the removal of pollutant gases.

In particular, the coating or the coated article may be used for the removal of pollutant gases in external conditions, and especially conditions where the coating is exposed to UV radiation (e.g., from sunlight).

The coating or the coated article may be used for the removal of pollutant gases in external conditions, and especially conditions where the coating is exposed to UV radiation (e.g., sunlight), over the long term, e.g., over time frames of 1000 hours or more, or 2000 hours or more, or 5000 hours or more, e.g., 10,000 hours or more, or 20,000 hours or more, or 50,000 hours or more.

As the skilled person will be aware, gases build up in the interior of road tunnels and there can be a high percentage of pollutants in the environment around any building or structure, including tunnels, that is located near to roads with high-traffic density. Tunnels and other structures and buildings may be lit using fluorescent bulbs, which emit UV radiation, as well as such structures and buildings being exposed to sunlight.

The coating composition of the present disclosure could therefore be used to coat the exterior surfaces of tunnels or buildings or other structures, especially those located near to roads with high-traffic density, where there is known to be a high percentage of pollutants in the environment (e.g., NOx gases from diesel vehicles).

The composition of the present disclosure could also be used to coat the interior surfaces of tunnels or buildings, especially those located near to roads with high-traffic density, where there is known to be a high percentage of pollutants in the environment (e.g., NOx gases from diesel vehicles). In practice, interior locations such as tunnels and buildings will normally be lit using bulbs which emit a UV component.

The composition of the present disclosure could be used to coat the exterior surfaces of power stations or buildings located near to power stations, or buildings in city centers, where there are known to be significant levels of NOx gases in the environment due to the power station emissions.

The composition of the present disclosure could be used to provide a coating inside residential or commercial buildings, where volatile organic compounds may be present.

The specific mesoporous titania particles required by the present disclosure have been found to have excellent capacity for removing pollutant gases from the atmosphere. Surprisingly, it has been found that the mesoporous titania particles do not degrade polymeric material in the coating and so have a low impact on coating surface integrity and appearance. The coating does not exhibit significant weight loss, color loss or gloss deterioration even when exposed to weathering conditions for prolonged periods of time.

Consequently, in an eighth aspect, there is provided the use of the coating as described in the second aspect of the disclosure, or the article as described in the fifth aspect of the disclosure, to provide a coating which both (a) is resistant to aesthetic and/or functional deterioration and (b) acts to improve the quality of the atmosphere.

Products according to the present disclosure have been shown to have NOx abatement comparable with that of coatings based on a commercial photocatalyst and considerably better than coatings based on pigmentary anatase, even after prolonged weathering.

Furthermore, optical performance of paints prepared in accordance with the present disclosure was comparable with, or even slightly better than, that of the commercial UV protector, both in terms of color changes ($\Delta E$) and gloss retention.

The problem of providing a UV protector for paints which also provides a remediation function for atmospheric pollutants has thus been solved by the present invention.

The products, uses and methods of the present disclosure allow pollutants, such as air pollutants, to be photocatalytically decomposed. The pollutants may, in particular, be selected from nitrogen oxides (NOx) and volatile organic compounds (VOC) and combinations thereof. In an embodiment, the products, uses and methods of the present disclosure can, for example, allow levels of NOx compounds (NO and/or $NO_2$) to be reduced.

The coating composition of the present disclosure can be used to form a coating that can reduce the concentration of pollutant gases in the environment. The coating composition comprises polymeric material together with mesoporous titania particles, wherein the particles have a continuous exterior convex surface and a particle diameter of greater than or equal to 1 μm but less than or equal to 50 μm, and a BET specific surface area of from 30 $m^2/g$ to 350 $m^2/g$, and a modal pore diameter of greater than or equal to 5 nm but less than or equal to 50 nm, and a pore size distribution such that 85% or more of the total pore volume is associated with pores with a diameter of 10 microns or less, wherein the coating composition comprises from 0.01% to 10% by volume of the particles, relative to the total volume of the coating composition and comprises from 5% to 99.99% by volume of polymeric material, relative to the total volume of the coating composition.

In an embodiment, the amount of mesoporous titania particles in the coating composition can, for example, be from 0.01% to 8% by volume, such as from 0.01% to 5% by volume, or from 0.01% to 3% by volume, or from 0.01% to 2%, by volume, relative to the total volume of the coating composition. In another embodiment, the amount of mesoporous titania particles in the coating composition can, for example, be from 0.02% to 5% by volume, such as from 0.05% to 4% by volume, or from 0.1% to 3% by volume, or from 0.2% to 2%, by volume, relative to the total volume of the coating composition. In yet another embodiment, the amount of mesoporous titania particles in the coating composition can, for example, be from 0.5% to 3% by volume, such as from 0.5% to 2% by volume or from 0.5% to 1% by volume.

In an embodiment, the coating composition can, for example, comprise from 0.1% to 5% by volume of the particles, relative to the total volume of the coating composition, and can, for example, comprise from 5% to 99.9% by volume of polymeric material, relative to the total volume of the coating composition.

In an embodiment, the coating composition can, for example, comprise from 0.5% to 3% by volume of the particles, relative to the total volume of the coating composition and can, for example, comprise from 5% to 99.5% by volume of polymeric material, relative to the total volume of the coating composition.

In an embodiment, the mesoporous titania particles and the polymeric material can, for example, be mixed together.

In an embodiment, the mesoporous titania particles can, for example, be dispersed throughout the coating composition; suitably they are substantially uniformly dispersed throughout the coating composition.

A coating as formed from the composition will therefore have the mesoporous titania particles dispersed throughout the coating. There may thus be bulk incorporation of the particles.

In an embodiment, the mesoporous titania particles and the polymeric material can, for example, not be mixed together.

In an embodiment, the mesoporous titania particles can, for example, be provided so that, when a coating is formed from the coating composition, the mesoporous titania particles are provided at the surface of the coating. For example, it may be that all the other components of the coating apart from the titania particles are applied as a layer to a surface and the mesoporous titania particles can then be applied on top of that layer. In an embodiment, they can, for example, be dusted on top of that layer. Any method of providing the particles as an outer layer of the coating can, however, be utilized. Known techniques such as coextrusion or lamination may be utilized to provide a layer of titania particles as an outer layer of the coating.

The present disclosure uses mesoporous titania particles which are not pigmentary titanium dioxide and which are not conventional ultrafine titanium dioxide.

As noted above, the modal pore diameter is greater than or equal to 5 nm but less than or equal to 50 nm, e.g., greater than or equal to 5 nm but less than or equal to 40 nm. In an embodiment, the modal pore diameter can, for example, be from 6 nm to 45 nm, such as from 7 nm to 45 nm, e.g., from 10 nm to 40 nm. In an embodiment, the modal pore diameter can, for example, be greater than or equal to 5 nm but less than or equal to 30 nm.

Pore diameter may suitably be measured using mercury intrusion porosimetery, e.g., using a Micromeritics® MicroActive AutoPore V 9600 porosimeter. Pore diameter may alternatively be measured using nitrogen isotherms (for pore diameters in the nanometer range), e.g., using a Micromeritics TriStar 3020™ machine. The skilled person is readily able to determine the modal pore diameter using such equipment.

In an embodiment, the modal pore diameter can, for example, be greater than or equal to 5 nm but less than or equal to 25 nm, e.g., greater than or equal to 5 nm but less than or equal to 23 nm, or greater than or equal to 5 nm but less than or equal to 22 nm. In an embodiment, the modal pore diameter is from 6 nm to 25 nm, such as from 7 nm to 25 nm, e.g., from 8 nm to 25 nm.

In an embodiment, the modal pore diameter can, for example, be greater than or equal to 5 nm but less than or equal to 20 nm, e.g., greater than or equal to 5 nm but less than or equal to 19 nm, or greater than or equal to 5 nm but less than or equal to 18 nm. In an embodiment, the modal pore diameter can, for example, be from 6 nm to 20 nm, such as from 7 nm to 20 nm, e.g., from 8 nm to 20 nm.

As noted above, the mesoporous titania particles have a pore size distribution such that 85% or more of the total pore volume is associated with pores with a diameter of 10 microns or less, such as 86% or more of the total pore volume, or 87% or more of the total pore volume, or 88% or more of the total pore volume, or 89% or more of the total pore volume.

In an embodiment, from 85% to 99.9% of the total pore volume can, for example, be associated with pores with a diameter of 10 microns or less, such as from 86% to 99.5% of the total pore volume, or 87% to 99% of the total pore volume.

The pore volume associated with pores of a stated diameter, e.g., those pores having a diameter of 10 microns or less, may suitably be measured using mercury intrusion porosimetery, e.g. using a Micromeritics® MicroActive AutoPore V 9600 porosimeter.

It will be appreciated by the skilled person that such porosimeter equipment can be used to provide information regarding the total pore volume of a sample of particles as well as information regarding the distribution of that pore volume over a range of pore sizes. The skilled person would therefore be able to determine the percentage of the total pore volume that is provided by pores in a defined size range, in this case those pores having a diameter of 10 microns or less.

The use of mesoporous titania particles where a large proportion of the pore volume is derived from pores having a diameter of 10 microns or less gives rise to beneficial results, as compared to conventional porous titania materials where significantly less than 85% of the pore volume derives from pores having a diameter of 10 microns or less. The mesoporous titania particles according to the present disclosure can be incorporated into a coating to reduce the concentration of pollutant gases in the environment, e.g., from air or water near to the coating, and surprisingly, even after weathering (including exposure to intense UV radiation from sunlight), the coating does not experience significant weight loss, color fade or gloss deterioration.

In an embodiment, the mesoporous titania particles can, for example, have a pore size distribution such that 90% or more of the total pore volume is associated with pores with a diameter of 10 microns or less, such as 91% or more of the total pore volume, or 92% or more of the total pore volume, or 93% or more of the total pore volume, or 94% or more of the total pore volume. It may be that the mesoporous titania particles have a pore size distribution such that 95% or more of the total pore volume is associated with pores with a diameter of 10 microns or less.

It may be that the mesoporous titania particles used in the present disclosure have a total pore volume of 0.8 ml/g or less, such as 0.75 ml/g or less, or 0.7 ml/g or less. Optionally, in an embodiment, the mesoporous titania particles used in the present disclosure can, for example, have a total pore volume of 0.65 ml/g or less, such as 0.6 ml/g or less, or 0.55 ml/g or less.

In an embodiment, the total pore volume is 0.5 ml/g or less, such as 0.45 ml/g or less, or 0.4 ml/g or less. In an embodiment, the total pore volume can, for example, be from 0.05 to 0.65 ml/g, such as from 0.1 to 0.6 ml/g or from 0.15 to 0.55 ml/g or from 0.2 to 0.5 ml/g or from 0.2 to 0.45 ml/g.

The total pore volume may suitably be measured using mercury intrusion porosimetery, e.g., using a Micromeritics® MicroActive AutoPore V 9600 porosimeter.

The titania particles used in the present disclosure are sized so as to be larger than nanoparticles. The mesoporous titania particles used in the present invention are therefore mesoporous particles having a particle diameter of 1 μm or more. As noted above, the particle diameter is greater than or equal to 1 μm but less than or equal to 50 μm. It may be greater than or equal to 1 μm but less than or equal to 40 μm, or greater than or equal to 1 μm but less than or equal to 35 μm, or greater than or equal to 1 μm but less than or equal to 30 μm.

The particle diameter (particle size) may suitably be determined by laser diffraction and may be measured using a laser diffraction machine, such as those available from Malvern Instruments Ltd, a MasterSizer® machine. The particle diameter (particle size) may alternatively be determined by X-ray sedimentation and may be measured using a X-ray disc centrifuge, such as those available from Brookhaven, e.g., a BI-XDC machine.

In an embodiment, the particle diameter can, for example, be 1.1 µm or more, 1.2 µm or more, 1.3 µm or more, 1.4 µm or more, 1.5 µm or more, 1.6 µm or more, 1.7 µm or more, 1.8 µm or more, or 1.9 µm or more. The particle diameter may be 2 µm or more.

In some embodiments, the mesoporous titania particles can, for example, have a particle diameter of from 1.5 µm to 45 µm, such as from 1.5 µm to 35 µm, e.g., from 1.5 µm to 20 µm or from 1.5 µm to 15 µm, such as from 1.5 µm to 12 µm.

In some embodiments, the mesoporous titania particles can, for example, have a particle diameter of from 2 µm to 35 µm, such as from 2 µm to 30 µm. In some embodiments, the mesoporous titania particles can, for example, have a particle diameter of from 2 µm to 25 µm, such as from 2 µm to 20 µm, e.g., from 2 µm to 15 µm or from 2 µm to 12 µm. The particles can, for example, have a diameter of 20 µm or less, such as from 2 to 20 µm.

The particle diameter is a geometric weight mean value for the particle diameter size (appropriate for the approximately log normal distribution which is often found with such particles).

As one skilled in the art is aware, crystal size is distinct from particle size. Crystal size relates to the size of the fundamental crystal units having internally consistent lattice planes, which make up the particulate material. The particle size is affected by factors such as the crystal size and incomplete fusion of crystals, as well as milling techniques used during production, such as dry, wet or incorporative milling, and subsequent treatments including deliberate treatments that cause aggregation of crystals.

The crystal size and particle size of the titanium dioxide may be determined by methods well known to those skilled in the art. For example, the crystal size may be determined by transmission electron microscopy on a sample with image analysis of the resulting photograph. The results of the crystal size may further be validated by reference to lattice spacing information, which is widely available in the literature. As noted above, a method which may be used for determining the particle size of the titanium dioxide is laser diffraction. X-ray sedimentation may alternatively be used.

The particle size of titanium dioxide may therefore in general be greater than or about equal to the crystal size. For the particles utilized in the present disclosure, the particle diameter is greater than the crystal size, e.g., at least 2×, or at least 3×, or at least 5× greater than the crystal size. In this regard, the particles used in the disclosure may have a particle size that is at least an order of magnitude greater than the crystal size, i.e., at least 10× greater than the crystal size. In an embodiment, the particles used in the disclosure have a particle size that can, for example, be at least 100× greater than the crystal size, or at least 1000× greater than the crystal size.

In an embodiment, the crystal size can, for example, be less than or equal to 5 nm and the particle size is greater than or equal to 1 micron and up to and including 50 microns, e.g., greater than or equal to 2 microns and up to and including 50 microns.

As noted above, the particles have a BET specific surface area of from 30 $m^2/g$ to 350 $m^2/g$. In an embodiment, the particles can, for example, have a BET specific surface area of 50 $m^2/g$ or more, such as from 50 to 320 $m^2/g$, or from 50 $m^2/g$ to 250 $m^2/g$. The particles can, for example, have a BET specific surface area of 70 $m^2/g$ or more, such as from 70 to 320 $m^2/g$, or from 70 $m^2/g$ to 250 $m^2/g$.

The specific surface area may be determined using the Brunauer, Emmett and Teller method (BET method) as described in J. Am. Chem. Soc., 1938, 60, 309.

In an embodiment, the mesoporous titania particles can, for example, have a specific surface area which is greater than 75 $m^2/g$. In one such embodiment, the particles can, for example, have a BET specific surface area of from 75 $m^2/g$ to 350 $m^2/g$, such as from 75 $m^2/g$ to 320 $m^2/g$, or from 75 $m^2/g$ to 250 $m^2/g$ or from 75 $m^2/g$ to 240 $m^2/g$.

In an embodiment, the mesoporous titania particles can, for example, have a specific surface area which is greater than or equal to 80 $m^2/g$. In one such embodiment, the particles can, for example, have a BET specific surface area of from 80 $m^2/g$ to 350 $m^2/g$, such as from 80 $m^2/g$ to 320 $m^2/g$, or from 80 $m^2/g$ to 250 $m^2/g$ or from 80 $m^2/g$ to 240 $m^2/g$.

The mesoporous titania particles may, in some embodiments, have a specific surface area of greater than 125 $m^2/g$, e.g., of 150 $m^2/g$ or higher, or 175 $m^2/g$ or higher. In an embodiment, they can, for example, have a specific surface area of 200 $m^2/g$ or higher, such as 210 $m^2/g$ or higher, or 220 $m^2/g$ or higher, or 225 $m^2/g$ or higher.

In an embodiment, they can, for example, have a specific surface area of 230 $m^2/g$ or higher, such as 235 $m^2/g$ or higher, or 240 $m^2/g$ or higher or even 250 $m^2/g$ or higher.

The specific surface area for the mesoporous titania particles may, in an embodiment, be up to 330 $m^2/g$, or up to 320 $m^2/g$, or up to 300 $m^2/g$, or up to 250 $m^2/g$, or up to 240 $m^2/g$.

The particles have a continuous exterior curved (convex) surface. They may, for example, be spherical or toroidal. It may be that they are ellipsoids, e.g., a prolate (elongated) spheroid or an oblate (flattened) spheroid. In an embodiment, they can, for example, be spherical. They can, for example, be mesoporous beads.

WO 2015/040426 discusses the control of the morphology of titania particles, both in terms of the overall shape of the particles (e.g., spherical or toroidal, smooth outer surface or rough outer surface, dense or hollow) and in terms of pore size (which in turn will impact on the specific surface area). In particular, it describes the production of mesoporous titania particles and details the conditions that can be used to produce particles having a continuous exterior curved (convex) surface, which may, for example, be spherical or toroidal.

For example, the process for the production of titania particles, may comprise providing a titania sol, and then spray drying the sol to provide dried titania particles, wherein (i) the titania sol is produced from a $TiO_2$ containing slurry and the pH of the slurry is controlled to be 3 pH units or more from the iso-electric point of the titania, e.g., by the addition of peptizing agent, in order to reduce the extent to which the titania sol is flocculated, or (ii) the titania sol is produced from a $TiO_2$ containing slurry and the iso-electric point is adjusted to be 3 pH units or more from the pH of the slurry, e.g., by the addition of dispersant, in order to reduce the extent to which the titania sol is flocculated.

The present disclosure is not, however, limited to the production of the titania particles by such a process.

The skilled person would appreciate that it is possible to determine whether particles have a continuous exterior curved (convex) surface using scanning electron microscopy (SEM) to image the particles.

The following non-limiting protocol can be used to obtain images of intact particles using scanning electron microscopy, thereby allowing the skilled person to visually ascertain whether the particles have a continuous exterior curved (convex) surface:—

Double sided adhesive tape is applied to a microscope stub, such that one of the adhesive sides of the tape is facing upwards, so as to provide an adhesive surface on the stub. A sample of the particles is then dusted onto the adhesive surface on the stub. For example, the sample may be provided on a spatula and is then lightly dusted onto the adhesive surface on the stub by tilting or tapping the spatula to give a (barely perceptible) deposit of particles. The sample-dusted stub is then coated with conductive material (e.g., gold) according to normal practice; for example, sputter coating may be used to apply an ultra-thin coating of electrically-conducting metal (such as gold, gold/palladium, platinum, silver, chromium or iridium) onto the particles as provided on the stub. Sputtered films for SEM typically have a thickness range of from 2 to 20 nm. The thus-prepared stub is then introduced into a scanning electron microscope and an image of the particles is obtained.

The SEM image is visually assessed to determine whether the particles have a continuous exterior curved (convex) surface, e.g., it can be seen whether the particles are spherical or toroidal or ellipsoidal.

Figure 1:
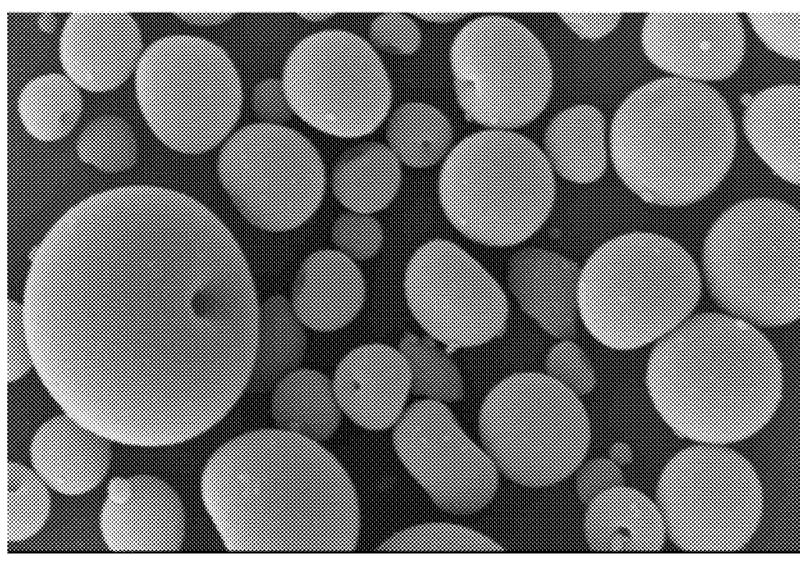
FIG. 1 shows a micrograph of mesoporous titania particles suitable for use in the present disclosure, as obtained by scanning electron microscopy (SEM).

FIG. 1 shows a micrograph of mesoporous titania particles suitable for use in the present disclosure, as obtained by scanning electron microscopy (SEM). It can be seen that the particles have a continuous exterior curved (convex) surface, with the particles being spherical. The particles may be considered as being mesoporous beads.

The mesoporous titania particles may optionally be treated, either by treatment of the titania material before it is formed into particles or after the particles have been formed, provided that the treated particles have a continuous exterior convex surface and a particle diameter of greater than or equal to 1 µm but less than or equal to 50 µm, a BET specific surface area of from 30 $m^2/g$ to 350 $m^2/g$, and a modal pore diameter of greater than or equal to 5 nm but less than or equal to 50 nm, and a pore size distribution such that 85% or more of the total pore volume is associated with pores with a diameter of 10 microns or less.

For example, coating, doping and calcination are all envisaged as possible treatments. One or more treatment may be used.

In general, the particles (e.g., prepared as described in WO2015/040426) may be treated before incorporation into the coating composition. This treatment may be applied by any of the known methods of applying a coating chemically to a pigment surface for the purpose of improving durability.

In an embodiment, the particles can, for example, be provided with a gas permeable coating. This can serve to provide a physical spacing between the $TiO_2$ particles and the polymer while allowing gas molecules to enter the porous structure of the particles. This may be particularly beneficial in assisting with the coating (a) being resistant to aesthetic and/or functional deterioration and (b) acting to improve the quality of the atmosphere.

Accordingly, in an embodiment, the mesoporous titania particles can, for example, be coated with ultrafine particles of an insulating material (such as silica) prior to incorporation into the coating composition (e.g., paint or polymeric coating).

The insulating particles may simply be admixed with the mesoporous titania particles to provide the coating on the mesoporous titania particles, or they may be heteroflocculated.

In an embodiment, the particles can, for example, be partially or fully encapsulated by a coating, such as an inorganic oxide coating, e.g., by silica. It may be that 80 wt % or more, such as 90 wt % or more, or 95 wt % or more, or 99 wt % or more, of the outer surface of each particle is covered in a coating such as silica. The coating may be silica so as to further reduce any residual photo-catalytic tendency of the mesoporous titania particles.

Coating of the particles with silica or other coatings may be achieved by known techniques. For example, a stable nano silica sol may be mixed with the $TiO_2$ sol from which the titania particles are to be formed and this mixture can then be spray dried. This would result in a titania particle encapsulated in silica, due to the smaller silica nano particles migrating to the outer edge of the droplet in the spray drying process. This would provide titania particles fully encapsulated in silica. Alternatively, the titania particles could be formed and then re-dispersed in an aqueous medium; a nano silica sol could then be added to provide a silica coating on the particles. The coated particles can then optionally be dried.

In an embodiment, the titania particles can, for example, be doped. This may be with metals, such as Fe, Cr, Mn, Ce, Ni, Cu, Sn, Al, Pb, Ag, Zr, Zn, Co, Mo and W, and/or non-metals such as B, C, N, P, As, S, Se, Te, F, Cl, Br and I. These lists of dopants are exemplary rather than limiting; other dopants such as Pd, Ru, Os, La, Er, V and the like can also be envisaged.

Doping with such elements can cause an increase in the catalytic properties and/or a decrease in the catalytic properties. It is therefore possible to improve the UV protection, due to a change in band gap to reduce the photo-catalysis. Doping can be achieved by known techniques. For example, a co-precipitation can be used to dope transition metals into the titanium dioxide lattice, whereby a dopant is added to the titanium sulfate liquor; this is then precipitated out resulting in doped titania.

In an embodiment, the titania can, for example, be subject to calcination. This can act to fuse adjacent crystallites while maintaining the anatase crystal form. The resulting particles though fused, retain dimensions in the ultrafine range.

The coating composition of the present disclosure may take a variety of forms. In an embodiment, the coating composition can, for example, be a paint. In another embodiment, the coating composition can, for example, be a polymeric coating material. In another embodiment, the coating composition can, for example, be a sun screen.

The skilled person will appreciate that the particles may be provided within the coating composition by bulk incorporation, but that this is not essential. Thus, it may, for example, be the case that the particles are applied as a layer. In an embodiment, a technique such as coextrusion or lamination can, for example, be used to apply a layer of the particles to the coating composition. This may, in particular, be useful for embodiments where the coating composition is a polymeric coating material and a technique such as coextrusion or lamination can be used to apply a layer of the particles to the bulk polymer to avoid the cost of bulk incorporation into the polymer.

In an embodiment, the coating composition can, for example, be in fluid, e.g., liquid, form, such as a paint. In another embodiment, the coating composition can, for example, be in powdered form or in the form of a flexible solid layer than can be applied to a surface.

In an embodiment, the polymeric material can, for example, be or comprise a synthetic or natural resin. Suitable plastics resins include general-purpose resins such as polyolefin resins, polyvinyl chloride resins, ABS resins, polystyrene resins and methacrylic resins; and engineering plastics resins such as polycarbonate resins, polyethylene terephthalate resins and polyamide resins. It may be or comprise a resin binder for paint, such as an acrylic resin, polyurethane resin, polyester resin, melamine resin, or epoxy resin. In one example, it is or comprises a polyester resin such as alkyd resin.

In an embodiment, therefore, the polymeric material can, for example, be or comprise a binder, which may, for example, be an organic polymeric binder, such as an acrylic polymer binder or an acrylic copolymer binder.

Binders may include, without limitation, synthetic or natural resins such as alkyds, acrylics, vinyl-acrylics, vinyl acetate/ethylene (VAE), polyurethanes, polyesters, melamine resins, epoxy resins, or oils.

In an embodiment, the coating composition can, for example, further comprise an aqueous carrier or solvent, such as water, and/or a non-aqueous carrier or solvent, such as an organic carrier or solvent. The carrier or solvent may, for example, be an aliphatic solvent, aromatic solvent, alcohol, or ketone.

The coating composition may further comprise one or more additives. Additives that can used in the coating composition may include, without limitation, additives to modify surface tension, improve flow properties, improve the finished appearance, increase wet edge, improve pigment stability, impart antifreeze properties, control foaming, control skinning, thickeners, stabilizers, emulsifiers, texturizers, adhesion promoters, UV stabilizers, flatteners (de-glossing agents) and the like.

The coating composition of the present disclosure may be applied to a surface by any known method, for example, by spraying (e.g., air or rotary-atomized), dipping, rolling, brushing, or the like. In an embodiment, the coating composition can, for example, be sprayed onto a surface to form a layer.

The mesoporous titania particles used in the present disclosure can be made in accordance with the process described in WO2015/040426, the disclosure of which is incorporated herein by reference.

As noted above, the titania may optionally be doped. A process as described in WO2015/040426, but including a doping step, may thus be utilized.

The process for preparing mesoporous titania particles may firstly involve the provision of a titania sol. A titania sol is a colloidal suspension of $TiO_2$ particles. The titania sol may be obtained by preparing a pulp via a sulfate process (e.g., with a Mecklenburg or Blumenfeld precipitation).

The pulp is then neutralized (e.g., with aqueous ammonia). The material is washed free from sulfates.

The slurry is then peptized (e.g., using hydrochloric acid). The iso-electric point of the titania is lowered (e.g., with the addition of citric acid).

The slurry may then be neutralized (e.g., with monoisopropanolamine)

Once a suitable deflocculated sol has been provided, the sol is then subjected to a drying process.

The temperature used during the drying step can be controlled so as to control the morphology of the resultant dried titania particles. The temperature can, for example, be controlled so as to control the particle shape of the resultant dried titania particles. A higher drying temperature results in toroidal (doughnut shaped) particles and a lower drying temperature results in more spherically shaped particles.

Before incorporation into the coating composition, the particles may have any residual acid removed. For example, they may be calcined or they may be irradiated with UV rays to remove residual acid (e.g. citric acid) from the production process.

In an embodiment, this treatment involves one of two processes: (a) calcination at a temperature of 400 to 600 degrees C., e.g., for six to ten hours or (b) irradiation of the particles with UV rays at an intensity of 5 to 15 $W/m^2$, e.g., for 60 to 90 hours.

As noted above, treatments of the particles are envisaged. The particles may thus optionally be calcined and/or coated with any suitable chemical or particulate by any means known in the art.

The present invention will be further illustrated by the following non-limiting examples.

EXAMPLES

Example 1—Production of Mesoporous Titania Particles

Mesoporous titania particles were obtained in accordance with the process described in WO2015/040426.

In this regard, pulp from a sulfate process was neutralized and washed free of sulfate. HCl was added to peptize the pulp and citric acid was added to shift the iso-electric point. Monoisopropanolamine was then added to raise the pH to around 7 whereupon a clear sol was seen to have been generated. The clear neutral sol was spray dried under controlled conditions. Specifically, the concentrated sol was then fed to a spray drier at 17 wt % solids at 110° C. using a Lab Plant Super 7 laboratory spray drier, to produce mesoporous titania particles.

The mesoporous titania particles were treated to remove the citric acid. Treatment involved one of two processes: (a) calcination at a temperature of 500 degrees C. for eight hours or (b) irradiation of the particles with UV rays for 72 hours at an intensity of 10 $W/m^2$.

The titania particles were mesoporous spherical beads. They had characteristics as set out in Table 1. These characteristics were measured as follows:

Particle Size

Roughly 1 g of sample was dispersed in 30 ml of 0.5% sodium silicate solution. Dispersion was carried out by stirring alone (no milling or high speed dispersion was used). A number of drops of dispersed sample were then dropped into the sample holder of a Malvern MasterSizer laser diffraction particle size analyzer until the correct level of optical attenuation was registered according to the instrument instructions. The correct Malvern installed calculation protocol was selected, depending on the crystal form of the titania: rutile "3_YYX" or anatase "3_ANA318" and measurements were taken.

Pore Characteristics

All pore characteristics (Modal Pore Size, Associated Pore Volume and % of Pore Volume associated with pore diameters of 10 microns or less) were measured by MCA Services of Cambridge UK, using a Micromeritics® MicroActive AutoPore V 9600 porosimeter to measure pore characteristics using mercury intrusion porosimetery, according to their procedure SC11.

BET Surface Area 0.3-0.4 g of sample was weighed accurately and degassed at 300 degrees C. for 30 minutes using a Micromeritics® Flowprep 060 degas system. The multipoint BET surface area was then measured using a Micromeritics® Gemini VII 2390a surface area analyzer.

In addition, commercially available products were provided:
Commercial anatase pigment: Tioxide® A-HR pigment (available from Huntsman P&A UK Ltd)
Commercial ultrafine titania photocatalyst: PC6A (available from Huntsman P&A UK Ltd)
Commercial alumina and stearic acid coated ultrafine rutile photoprotector: UVTitan® M160 pigment (available from Merck)

TABLE 1

Titania particles as provided in Example 1 for use in testing in subsequent examples

| | Particle Diameter (μm) | Modal Pore Size (nm) | Total Associated Pore Volume (ml/g) | Pore volume associated with pore diameters of 10 microns or less (%) | BET SSA ($m^2/g$) |
|---|---|---|---|---|---|
| Calcined Particles (Inventive) | 10.95 | 17.6 | 0.3612 | 96.8 | 80 |
| UV Irradiated Particles (Inventive) | 10.75 | 9.1 | 0.3446 | 96.6 | 234 |
| Tioxide ® A-HR (Comparative) | 0.82 | 245.4 | 0.6667 | 70.9 | 8 |
| Ultrafine PC6A (Comparative) | 54.49 | 58.7 | 0.5779 | 51.5 | 246 |
| UV Titan M160 (Comparative) | 38.41 | 26.8 | 0.6631 | 52.3 | 72 |

These products differ greatly in terms of pore size distribution. The mesoporous products of the present invention have two sharp peaks, corresponding to intra bead voids and inter bead voids, respectively. The quoted value for the modal pore size and associated pore volume is for the intra bead void. The non-mesoporous particle types of the prior products have a less ordered structure and therefore have one or more broad peaks. The quoted value for the modal pore size and associated pore volume is for the main peak for each sample.

The calcined and UV irradiated particles according to the present invention were spherical beads, as could be seen by scanning electron microscopy (SEM).

Example 2—Production of Paints Containing Mesoporous Titania Particles

A paint base was prepared according to Appendix 1 and was then used with particles as set out in Table 1 above.

For the 'Blank' paint (Sample 1) no pigment was added.

For Sample 2, no pigment was added in forming the paint base, but instead conventional pigmentary anatase titania (Tioxide® A-HR pigment from Huntsman P&A UK Ltd) was provided as a layer on top of the paint base, in the manner as described below.

For Sample 3, no pigment was added in forming the paint base, but instead conventional ultrafine anatase titania (PC6A from Huntsman P&A UK Ltd) was provided as a layer on top of the paint base, in the manner as described below.

For Sample 4, the UV irradiated mesoporous titania as obtained in Example 1, option (b) was added as the pigment.

For Sample 5, no pigment was added in forming the paint base, but instead the UV irradiated mesoporous titania as obtained in Example 1, option (b) was provided as a layer on top of the paint base, in the manner as described below.

For Sample 6, no pigment was added in forming the paint base, but instead the calcined mesoporous titania as obtained in Example 1, option (a) was provided as a layer on top of the paint base, in the manner as described below The paints were applied to metal plates.

For Samples 1 and 4, the paints as prepared provided the coating.

For Samples 2, 3, 5 and 6, the paints as prepared provided a first layer and the titania was then dusted as a second layer onto the surface of that first layer while the first layer was still wet. The coating was the combination of the first layer and the second layer.

Example 3—Ability to Remove NO Gas

The coated metal plates as prepared in Example 2 were weighed before weathering in a xenon arc weathering cabinet for 1000 hours.

At 1000 hours, the weight loss was measured and the panels were also tested to assess their ability to remove NO gas from 1000 ppb NO gas stream, according to ISO22197-1 at a flow rate of 1.5 liters/minute.

The results are shown in Table 2 below.

TABLE 2

| | | ABSOLUTE | | RELATIVE (Versus blank) | |
|---|---|---|---|---|---|
| | | Polymer Degradation mg/g | NO removed ppb/1000ppb | Polymer Degradation Delta mg/g | NO removed Delta ppb |
| 1 | Blank | 569 | 16 | — | — |
| 2 | Pigmentary Anatase (Comparative) | 1604 | 33 | 1035 | 17 |
| 3 | Ultrafine Anatase (Comparative) | 1040 | 825 | 471 | 809 |
| 4 | Mesoporous (Irradiated, Dispersed) (Inventive) | 595 | 513 | 26 | 497 |
| 5 | Mesoporous (Irradiated, Dusted) (Inventive) | 575 | 516 | 6 | 500 |
| 6 | Mesoporous (Calcined, Dusted) (Inventive) | 555 | 486 | −14 | 470 |

The samples according to the present invention (Samples 4, 5 and 6) resulted in significantly lower paint weight loss than the samples using conventional (non-mesoporous) titania (Samples 2 and 3) after the same exposure. The weight losses from these samples were similar to the blank sample (Sample 1: resin only).

It can thus be seen that, surprisingly, the products that comprise mesoporous titania according to the present invention (Samples 4, 5 and 6), which is a high surface area anatase, are significantly less harmful than those comprising pigmentary anatase in terms of photodegradation of the polymeric resin of the paint.

It will be appreciated by the skilled person that anatase generally gives more problematic photocatalysis than rutile. In addition, the tendency towards film degradation (irrespective of crystal form) becomes more marked with increasing surface area.

Furthermore, it will be noted that the tested samples according to the present invention (Samples 4, 5 and 6) display significant NO gas removal from the 1000 ppb gas stream. This ability to remove the pollutant gas is significantly better than the sample with pigmentary anatase (Sample 2) as well as the blank sample (resin only).

Although the effect on pollutant gas is not quite as pronounced as the sample using conventional ultrafine anatase (sample 3), it will be appreciated by the skilled person that the measured removal of NO gas from the gas stream is still at a very significant level. Thus the effect is certainly sufficient to be industrially applicable and commercially useful.

The ability to remove the pollutant gas at significant and useful levels without deteriorating the polymer resin, and therefore without adversely impacting on the lifespan of the paint coating, is surprising and technically very beneficial. This is especially the case for applications where the coating would be used outdoors and therefore would be exposed to weathering conditions due to UV light from the sun. It would also be beneficial for applications where the coating is exposed to other sources of UV light, such as from fluorescent bulbs.

It is therefore apparent that the claimed products have the benefit of this unexpected combination of characteristics in terms of providing a coating which both (a) is resistant to aesthetic and/or functional deterioration and (b) acts to improve the quality of the atmosphere by removing pollutants.

Example 4—Colored Paints—Weathering and NOx Reduction

A selection of the titania materials reported in Table 1 were individually tested in red and blue paints tinted with organic pigments. Organic pigments are generally degraded on exposure to UV radiation, and the fade characteristics of paints containing such pigments provide a convenient measure of UV protection.

In this regard, a series of acrylic melamine formaldehyde paints was formulated according to Appendix 2, each containing $TiO_2$ together with a colored pigment: either DPP Red pigment (PR254) or Phthalocyanine Blue pigment (PB15:1). The formulations were such that the dry volume fraction of $TiO_2$ was 0.01 in each colored paint film and the dry volume fraction of colored pigment was 0.01 in each colored paint film.

Four $TiO_2$ materials from those set out in Table 1 above were used with each color of pigment:

Calcined mesoporous titania as obtained in Example 1, option (a) (referred to as "Meso")

UVTitan® M160 pigment available from Merck

PC6A available from Huntsman P&A UK Ltd

Tioxide® A-HR pigment available from Huntsman P&A UK Ltd

Each of the four materials was used in preparing a blue paint sample and a red paint sample; these were created by dispersing the $TiO_2$ material into the colored paint. A fifth sample for each of the red paint and the blue paint was created by forming the paint film and then sprinkling the mesoporous beads onto the freshly applied wet paint film. A total of ten paints were thus formulated.

An additional variant (labeled 'Resin Blank') contained no $TiO_2$ and no colored pigment.

Paint panels were tested for optical properties and NOx abatement performance and then weathered in an Atlas Weatherometer for 500 hours before being retested. They were then weathered up to a total of 1000 hours in the Atlas Weatherometer before being retested.

Table 3 below lists the variants and gives information on NOx abatement for the unweathered and weathered paints under test conditions prescribed in ISO22197 part 1. Mean values for the abatement results of each pair of samples prepared with each $TiO_2$ material are also shown in Table 3.

TABLE 3

| | % NOx Reduction | | |
|---|---|---|---|
| | 0 hrs | 500 hrs | 1000 hrs |
| Resin Blank | 0.3 | 0.2 | 0.1 |
| Meso + PB15:1 | 0.2 | 2.1 | 1.8 |
| Meso + PR254 | 0.2 | 4.7 | 3.4 |
| Mesoporous Mean | 0.2 | 3.4 | 2.6 |
| UV Titan + PB15:1 | 0.2 | 0.1 | 0.4 |
| UV Titan + PR254 | 0.6 | 0.2 | 0.3 |
| UVTitan Mean | 0.4 | 0.1 | 0.3 |
| Meso + PB15:1 sprinkled | 0.2 | 3.5 | 2.6 |
| Meso + PR254 sprinkled | 0.4 | 7.0 | 2.4 |
| Meso Sprinkled Mean | 0.3 | 5.2 | 2.5 |
| A-HR + PB15:1 | 0.4 | 0.4 | 0.3 |
| A-HR + PR254 | 0.4 | 0.4 | 0.4 |
| A-HR Mean | 0.4 | 0.4 | 0.3 |
| PC6A + PB15:1 | 0.2 | 2.9 | 10.5 |
| PC6A + PR254 | 0.5 | 6.2 | 2.5 |
| PC6A Mean | 0.4 | 4.5 | 6.5 |

It can be seen that the fresh paints (all variants) had little NOx abatement effect. However, after 500 hours of weathering, NOx abatement with the particles according to the present disclosure ("Meso" samples) was comparable with that of the commercial photocatalyst and considerably better than the pigmentary anatase. This trend continued after 1000 hours of weathering. As expected, the commercial UV protective $TiO_2$ (UV Titan, A-HR, and PC6A) had low NOx abatement effect (comparable to the Resin Blank).

Optical performance of the paints (color and gloss) was also affected by weathering. It can be seen in Table 4 below that the color changes ($\Delta E$) and gloss retention of the systems involving mesoporous particles according to the present invention were comparable (or in some cases slightly better than) those of the commercial UV protector. Mean values for the color change and gloss retention results of each pair of samples prepared with each $TiO_2$ material are also shown in Table 4.

TABLE 4

|   | | ΔE* | % gloss retained |
|---|---|---|---|
| 1 | Resin Blank | 1.68 | 61 |
| 2 | Meso + PB15:1 | 4.35 | 42 |
| 3 | Meso + PR254 | 6.02 | 35 |
|   | Mesoporous Mean | 5.18 | 38 |
| 4 | UV Titan + PB15:1 | 7.15 | 12 |
| 5 | UV Titan + PR254 | 4.92 | 23 |
|   | UVTitan Mean | 6.04 | 17 |
| 6 | Meso + PB15:1 sprinkled | 10.29 | 22 |
| 7 | Meso + PR254 sprinkled | 9.69 | 44 |
|   | Meso Sprinkled Mean | 9.99 | 33 |
| 8 | A-HR + PB15:1 | 17.13 | 3 |
| 9 | A-HR + PR254 | 22.50 | 14 |
|   | A-HR Mean | 19.81 | 9 |
| 10 | PC6A + PB15:1 | 26.33 | 2 |
| 11 | PC6A + PR254 | 23.13 | 7 |
|   | PC6A Mean | 24.73 | 5 |

The problem of providing a UV protector for paints which also provides a remediation function for atmospheric pollutants has thus been solved by the present invention.

Prophetic Example 5

Mesoporous titania particles were obtained in accordance with the process described in WO2015/040426.

In this regard, pulp from a sulfate process was neutralized and washed free of sulfate. HCl was added to peptize the pulp and citric acid was added to shift the iso-electric point. Monoisopropanolamine was then added to raise the pH to around 7 whereupon a clear sol was seen to have been generated. The clear neutral sol was spray dried under controlled conditions. Specifically, the concentrated sol was then fed to a spray drier at 17 wt % solids at 110° C. using a Lab Plant Super 7 laboratory spray drier, to produce uncalcined mesoporous titania particles.

A portion of the mesoporous titania particles was calcined at 500° C. for 8 hours to remove citric acid resulting in calcined mesoporous beads.

The calcined and uncalcined beads were separately dispersed in water at pH 7. In each case, silica nanospheres (Ludox®-CL, available from Grace) equal to 0.1 wt % on $TiO_2$ was added to the dispersion.

The resulting silica coated titania particles were then spray dried in each case and incorporated into colored paints, where they each displayed both improved color fade (as compared to the uncoated material) and equivalent NOx reduction.

Appendix 1—Paint Preparation for Example 2

3000 g of 60% Synocryl® 826S solution was placed in a container with 1 liter of 63% Cymel UB-26-BX (available from Allnex) shaken thoroughly and then trundled for 2 hours to produce a millbase. Synocryl® 826S is a hydroxy functional acrylic resin, used in the formulation of low temperature stoving systems. It is available from Cray Valley as a 60% solution.

In the case of the "Mesoporous Dispersed" material, around 0.5 g of $TiO_2$ was added into around 20 milliliters of the prepared millbase and dispersed on a Speedmixer mixing machine for 30 seconds at 2500 rpm (Speedmixer manufactured by Hauschild).

In the cases of the Pigmentary Anatase, Ultrafine Anatase, Dusted Irradiated Mesoporous Beads and Dusted Calcined Mesoporous Beads, around 0.002 mg were dusted onto wet paint films approximately 10 cm×5 cm.

Appendix 2—Paint Preparation for Example 4

Milling Solution—20% Synocryl 826S

A 20% milling solution was prepared by trundling 60% Synocryl® 826S (200 g) with Xylene: Butanol 1:1 (400 g), and 4.3 g DisperByk 161 (wetting and dispersing additive from BYK) until well mixed.

Organic Tints

Tinter solutions were prepared for the red and blue paints as follows: 350 g Synocryl® 826S, 60%, 20 g Xylene, 40 g Disperbyk 163, 40 g organic pigment (PB15:1 Heliogen Blue K6911FP OR PR254Hosterperm Red D3G70) were shaken on a red devil for 1 hr with 2 kg of 6 mm steal ballotini.

The paints were prepared by the following method (using quantities in grams as set out in Table 5).

CYMEL® 651 resin is a partially n-butylated melamine crosslinker supplied at 60% solids in a mixture of n-butanol and xylene from Allnex.

The component numbers appear in the first column of Table 5 below.

Paint Make-Up $TiO_2$ components of the paint make up were in the form of the appropriate solids. All other components were solutions or suspension. Quantities added in grams of each component (quoted as weight of solid, solution or suspension) are given in Table 5 below.

$TiO_2$, Organic Tint and 20% Synocryl® 826S components (quantities in grams according to Table 5) were added to a glass jar, and trundled for 16 hrs with 170 g of 8 mm glass beads. A quantity of 60% Synocryl® 826S was added, and the paint shaken immediately to prevent pigment shock, followed by trundling for 30 minutes. A further portion of 60% Synocryl® 826S was added and an amount of 60% Cymel 651 solution, before trundling for at least an hour. The paint was then sieved, ready to use.

In the cases where the mesoporous beads were dusted over the paint, 0.0018 g of particles were used on a panel sized 10 cm×5 cm.

Although making and using various embodiments of the present invention have been described in detail above, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

TABLE 5

| Component | PC6a, red | PC6A, blue | Ultra Fine, red | Ultra Fine, blue | AHR, red | AHR, blue | Meso-Beads, red | Beso-Beads, blue | Resin Blank | Resin red | Resin blue |
|---|---|---|---|---|---|---|---|---|---|---|---|
| 1 $TiO_2$ | 2.9 | 2.8 | 2.4 | 2.4 | 2.9 | 2.9 | 2.2 | 2.2 | | | |
| 2 Organic Tint | 1.2 | 0.9 | 1.2 | 0.9 | 1.2 | 0.9 | 1.2 | 0.9 | | 1.2 | 0.9 |
| 3 20% Syn 826s | 21.0 | 21.0 | 21.0 | 21.0 | 21.0 | 21.0 | 21.0 | 21.0 | 28.0 | 21.0 | 21.0 |

TABLE 5-continued

| Component | PC6a, red | PC6A, blue | Ultra Fine, red | Ultra Fine, blue | AHR, red | AHR, blue | Meso-Beads, red | Beso-Beads, blue | Resin Blank | Resin red | Resin blue |
|---|---|---|---|---|---|---|---|---|---|---|---|
| 4  60% Syn 826s | 10.5 | 10.5 | 10.5 | 10.5 | 10.5 | 10.5 | 10.5 | 10.5 | 14.0 | 10.5 | 10.5 |
| 5  60% Syn 826s | 83.3 | 83.3 | 83.3 | 83.3 | 83.3 | 83.3 | 83.3 | 83.3 | 62.9 | 83.3 | 83.3 |
| 6  60% Cymel 651 | 36.0 | 36.0 | 36.0 | 36.0 | 36.0 | 36.0 | 36.0 | 36.0 | 28.8 | 36.0 | 36.0 |
| Total | 154.83 | 154.39 | 154.39 | 154.05 | 154.83 | 154.50 | 154.18 | 153.85 | 133.70 | 151.95 | 151.61 |

What is claimed is:

1. A coating composition suitable for use in forming a coating that can reduce the concentration of pollutant gases in the environment, the coating composition comprising:
   from 0.01 to 10% vol.-% of mesoporous titania particles, relative to a total volume of the coating composition; and
   from 5 to 99.99 vol.-% of a polymeric material, relative to the total volume of the coating composition,
   wherein,
   the mesoporous titania particles comprise:
      a continuous exterior convex surface,
      a particle diameter of ≥1 μm but ≤50 μm,
      a BET specific surface area of from 30 to 350 m$^2$/g,
      a modal pore diameter of ≥5 nm but ≤50 nm, and
      a pore size distribution so that 85% or more of a total pore volume is associated with pores having a diameter of 10 μm or less.

2. The coating composition as recited in claim 1, wherein the mesoporous titania particles comprise from 0.01 to 5 wt.-% of particulate silica.

3. The coating composition as recited in claim 1, wherein the coating composition comprises,
   from 0.1 to 5 vol.-% of the mesoporous titania particles, relative to the total volume of the coating composition, and
   from 5 to 99.9 vol.-% of the polymeric material, relative to the total volume of the coating composition.

4. The coating composition as recited in claim 1, wherein the modal pore diameter is ≥ to 5 nm but ≤ to 25 nm.

5. The coating composition as recited in claim 1, wherein the pore size distribution is such so that 90% or more of the total pore volume is associated with pores comprising a diameter of 10 μm or less.

6. The coating composition as recited in claim 1, wherein the total pore volume is 0.8 ml/g or less.

7. The coating composition as recited in claim 1, wherein the particle diameter is from 2 to 35 μm.

8. The coating composition as recited in claim 1, wherein the BET specific surface area is from 70 to 250 m$^2$/g.

9. The coating composition as recited in claim 1, wherein the mesoporous titania particles further comprise a spherical shape.

10. A coating formed from the coating composition as recited in claim 1, wherein the mesoporous titania particles are either dispersed within the coating or are present as a layer at an exterior face of the coating.

11. The coating as recited in claim 10, wherein the coating is provided on a surface which, in use, is exposed to an environment comprising pollutant gases.

12. The coating as recited in claim 11, wherein the surface, in use, is exposed to UV radiation.

13. A process for providing a coating on a surface, the coating being suitable for use in reducing a concentration of pollutant gases in an environment, the process comprising:
   providing a coating base comprising a polymeric material;
   applying the coating base to a surface so as to form a layer; and
   applying mesoporous titania particles to the layer so as to form a coating comprising the coating base and the mesoporous titania particles,
   wherein,
   the mesoporous titania particles comprise:
      a continuous exterior convex surface,
      a particle diameter of ≥1 μm but ≤50 μm,
      a BET specific surface area of from 30 to 350 m$^2$/g,
      a modal pore diameter of ≥5 nm but ≤50 nm, and
      a pore size distribution so that 85% or more of a total pore volume is associated with pores having a diameter of 10 μm or less,
   the coating comprises from 0.01 to 10 vol.-% of the mesoporous titania particles, relative to a total volume of the coating, and
   from 5 to 99.99 vol.-% of the polymeric material, relative to the total volume of the coating.

14. The process as recited in claim 13, wherein the coating base further comprises one or more further coating composition components selected from a carrier solvent and a carrier additive.

15. The process as recited in claim 13, wherein the mesoporous titania particles are applied to the layer by dusting the mesoporous titania particles onto the layer.

16. A process for providing a coating on a surface, the coating being suitable for use in reducing a concentration of pollutant gases in an environment, the process comprising:
   providing the coating composition as recited in claim 1; and
   applying the coating composition to a surface so as to form a layer.

17. The process as recited in claim 16, wherein the coating composition provided comprises the mesoporous titania particles mixed with the polymeric material.

18. The process as recited in claim 16, wherein the coating composition is provided by,
   providing a coating base comprising the polymeric material, and then
   dispersing the mesoporous titania particles in the coating base so as to form the coating composition.

19. The process as recited in claim 18, wherein the coating base comprising the polymeric material further comprises one or more further coating composition components.

20. The process as recited in claim 18, wherein, after the mesoporous titania particles have been dispersed in the coating base, one or more further coating composition components are added, so as to form the coating composition.

21. An article comprising a surface, at least a part of the surface being coated with a coating which is formed from the composition as recited in claim 1 so as to provide a coated surface.

22. The article as recited in claim 21, wherein,
the coating comprises the mesoporous titania particles being either dispersed within the coating or being present as a layer at an exterior face of the coating, and
at least a part of the surface of the article is coated with the coating comprising the mesoporous titania particles being either dispersed within the coating or being present as the layer at the exterior face of the coating.

23. The article as recited in claim 21, wherein,
the article further comprises an exterior surface, and
at least a part of the exterior surface is coated with the coating.

24. The article as recited in claim 21, wherein the article is a building or a part of the building.

25. The article as recited in claim 21, wherein the article is selected from a pavement, an automobile, a road surface, a road tunnel, an aircraft, a water vessel, a boat, a ship, a sign, fencing, decking, a sound-barrier, and a railing.

26. The article as recited in claim 21, wherein the article, in use, comprises at least one surface which is exposed to both pollutant gases and to UV radiation.

27. The article as recited in claim 26, wherein the UV radiation is from direct sunlight.

28. A method for removing pollutant gases from an environment, the method comprising:
providing the article as recited in claim 21; and
allowing the coated surface to contact the environment comprising the pollutant gases.

29. The method as recited in claim 28, wherein the coated surface is allowed to contact the environment comprising the pollutant gases in conditions where the coating is exposed to UV radiation from sunlight.

30. The method as recited in claim 28, wherein the coated surface is allowed to contact the environment comprising the pollutant gases over a time frame of 1,000 hours or more.

31. The method as recited in claim 30, wherein the time frame is 20,000 hours or more.

32. The method as recited in claim 28, wherein the coated surface is exposed to the UV radiation from sunlight over a time frame of 1,000 hours or more.

33. The method as recited in claim 32, wherein the time frame is 20,000 hours or more.

* * * * *